US00RE48838E

(19) United States
(12) Reissued Patent
Lund

(10) Patent Number: US RE48,838 E
(45) Date of Reissued Patent: Dec. 7, 2021

(54) SELF-LUBRICATING TAMPON APPLICATOR

(71) Applicant: Lacey Janell Lund, Rogers, AR (US)

(72) Inventor: Lacey Janell Lund, Rogers, AR (US)

(21) Appl. No.: 16/698,419

(22) Filed: Nov. 27, 2019

Related U.S. Patent Documents

Reissue of:
(64) Patent No.: 10,022,276
Issued: Jul. 17, 2018
Appl. No.: 15/730,840
Filed: Oct. 12, 2017

(51) Int. Cl.
*A61F 13/28* (2006.01)
*A61F 15/00* (2006.01)

(52) U.S. Cl.
CPC ..... *A61F 13/28* (2013.01); *A61F 15/003* (2013.01); *A61L 2300/30* (2013.01)

(58) Field of Classification Search
CPC ..... A61F 13/26; A61F 13/28
USPC ..... 604/12, 15
See application file for complete search history.

(56) References Cited

U.S. PATENT DOCUMENTS 3,139,886 A 7/1964 Tallman et al. ..... A61F 13/26 604/12
3,335,726 A 8/1967 Maranto ..... A61F 13/26 604/12
3,456,851 A 7/1969 Mattes et al.
3,724,465 A 4/1973 Duchane
4,312,348 A 1/1982 Friese ..... A61F 13/26 604/363
4,421,504 A * 12/1983 Kline ..... A61M 31/007 604/12
4,690,671 A 9/1987 Coleman et al. ..... A61F 13/26 604/12
5,676,647 A * 10/1997 Cimber ..... A61F 13/26 604/11
6,592,540 B2 7/2003 DeCarlo
6,746,418 B1 6/2004 Pauley et al.
7,666,160 B2 * 2/2010 Rajala ..... A61M 31/00 28/118

(Continued)

FOREIGN PATENT DOCUMENTS

CA 2470529 A1 * 7/2003 ..... A61M 31/00
CA 2602588 A1 3/2006

(Continued)

*Primary Examiner* — Cary E Wehner
(74) *Attorney, Agent, or Firm* — Dale J. Ream

(57) ABSTRACT

A self-lubricating tampon applicator includes a barrel having opposed insertion and proximal end portions and having a continuous side wall that defines an interior area and a plurality of spaced apart apertures and proximate the insertion end portion. A tampon is positioned in the interior area of the barrel. A piercing member is positioned between the tampon and the plurality of apertures. A lubricant reservoir is positioned between the tampon and the plurality of piercing members. A plunger situated in the barrel engages a proximal end of the tampon and is slidable from a starter configuration extending from the proximal end portion of the barrel to a deployed configuration positioned inside the barrel. Pressure applied to the plunger pushes the tampon and the reservoir downstream and the reservoir is pierced by the piercing member, dispensing lubricant through the plurality of apertures onto an outer surface of the barrel.

23 Claims, 16 Drawing Sheets

AMENDED

(56) References Cited

U.S. PATENT DOCUMENTS

| | | | | |
|---|---|---|---|---|
| 7,993,667 | B2 * | 8/2011 | Gehling | A61F 13/2085 424/431 |
| 2002/0026140 | A1 * | 2/2002 | McNamara | A61F 13/28 604/12 |
| 2002/0128590 | A1 * | 9/2002 | Decarlo | A61F 13/28 604/12 |
| 2002/0193726 | A1 * | 12/2002 | Cimber | A61F 13/26 604/11 |
| 2006/0004318 | A1 * | 1/2006 | Przepasniak | A61M 31/00 604/14 |
| 2015/0351974 | A1 * | 12/2015 | Levantino | A61F 13/266 604/57 |

FOREIGN PATENT DOCUMENTS

| | | | | |
|---|---|---|---|---|
| GB | 2277447 | A * | 11/1994 | A61F 13/263 |
| WO | WO-2012114200 | A2 * | 8/2012 | A61F 13/2077 |
| WO | WO-2014168470 | A1 * | 10/2014 | A61F 13/2097 |
| WO | WO-2019068351 | A * | 4/2019 | A61F 13/266 |

* cited by examiner

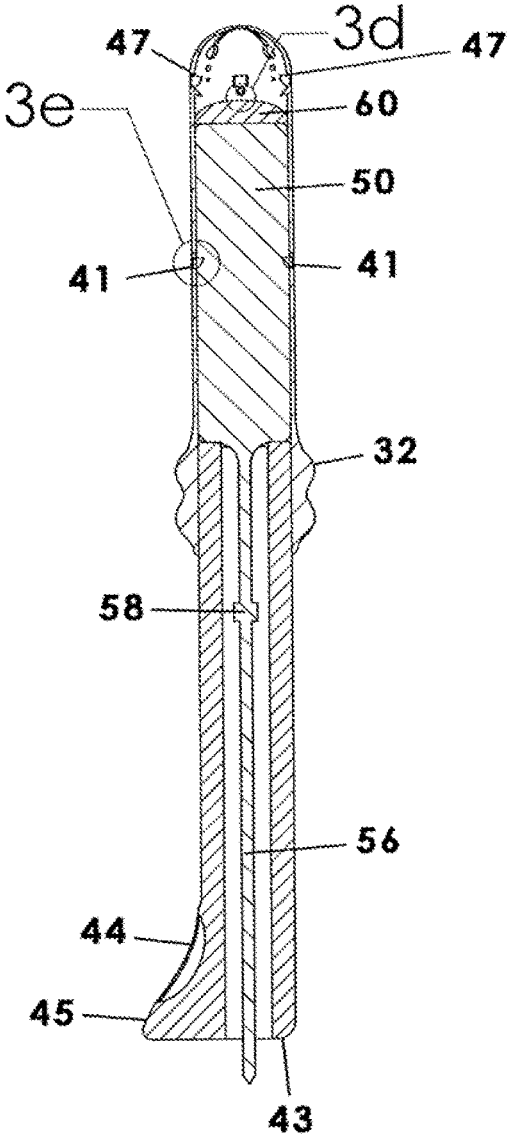
Fig. 3b
AMENDED

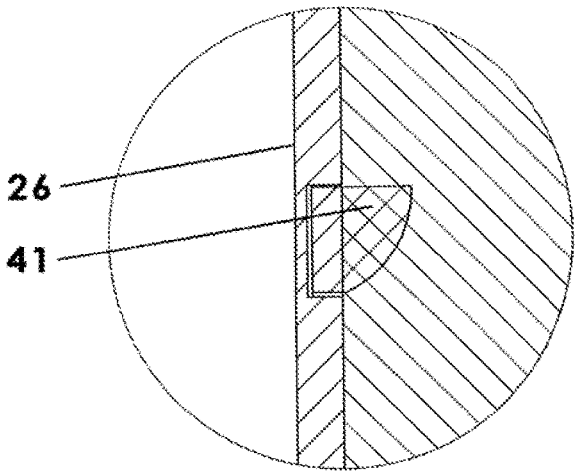
Fig. 3e
AMENDED

SELF-LUBRICATING TAMPON APPLICATOR

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

The present invention relates generally to tampon applicators and, more particularly, to a self-lubricating tampon applicator that dispenses a lubricant to an exterior wall of a barrel of the applicator simultaneously with the pushing of a tampon out of the barrel.

A tampon is a feminine hygiene product that includes a mass of absorbent material that is used to absorb a woman's menstrual flow. Most tampons are constructed of a combination of cotton and rayon. Using an applicator, the tampon is inserted into the woman's vagina during menstruation where is absorbs menstrual fluids and is then removed and, if necessary, is replaced with a fresh tampon.

Insertion of a tampon may be difficult or uncomfortable especially due to an absence of moisture in the vaginal tissues, especially in young women who are inexperienced in the insertion technique or when the menstruation cycle is subsiding. Various applicators and methods have been proposed for lubricating the tampon itself or the rounded tip of a tampon applicator (e.g. the barrel) to improve insertion difficulties. Specifically, the CA 2602588 patent proposes one or more fluid conduits in fluid communication with an outer surface of the applicator for delivering lubricant thereto when a lubricant reservoir is ruptured.

Although presumably effective for their intended uses, the existing products and proposals do not optimize the ease of use and effective lubrication needed to enhance the insertion of a tampon into a body cavity. Therefore, it would be desirable to have a self-lubricating tampon applicator for selectively dispensing lubricant onto an exterior surface of the applicator barrel simultaneously and incrementally as the tampon is dispensed.

SUMMARY OF THE INVENTION

A self-lubricating tampon applicator according to the present invention includes a barrel having an insertion end portion and a proximal end portion opposite the insertion end portion and having a continuous side wall extending therebetween that defines an interior area. The continuous side wall defines a plurality of apertures spaced apart from one another and proximate the insertion end portion. A tampon is positioned initially in the interior area of the barrel. The tampon applicator includes a plurality of piercing members coupled to an inner surface of the continuous side wall and spaced apart from one another in the interior area between the tampon and the plurality of apertures. A reservoir containing a lubricant is positioned in the interior area between the tampon and the plurality of piercing members.

A plunger is situated in the barrel having a first end engaging a proximal end of the tampon, the plunger having a cylindrical configuration selectively slidable from a starter configuration extending away from the proximal end portion of the barrel to a deployed configuration positioned in the interior area of the barrel. Pressure applied to the plunger pushes the tampon and the reservoir downstream within the interior area of the barrel and the reservoir is pierced by the piercing member, whereby the lubricant from the reservoir is dispensed through the plurality of apertures onto an outer surface of the barrel.

Therefore, a general object of this invention is to provide a self-lubricating tampon applicator for selectively dispensing lubricant onto an exterior surface of the applicator barrel as the tampon is dispensed.

Another object of this invention is to provide a self-lubricating tampon applicator, as aforesaid, having strategically positioned apertures through which lubricant is dispensed incrementally as a plunger deploys a tampon.

Still another object of this invention is to provide a self-lubricating tampon applicator, as aforesaid, having a finger guide member that enables a user to stabilize movement of the plunge.

Yet another object of this invention is to provide a self-lubricating tampon applicator, as aforesaid, that audibly "clicks" as the plunger is deployed so as to notify a user of an extent to which a tampon has been inserted.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 3b is a sectional view taken along line 3b-3b of FIG. 3a;

FIG. 3c is an isolated view on an enlarged scale taken from FIG. 3a;

FIG. 3d is an isolated view on an enlarged scale taken from FIG. 3a;

FIG. 3e is an isolated view on an enlarged scale taken from FIG. 3a;

FIG. 5b is an isolated view on an enlarged scale taken from FIG. 5a;

FIG. 7b is a sectional view taken along line 7b-7b of FIG. 7a;

FIG. 8b is a sectional view taken along line 8b-8b of FIG. 8a;

FIG. 10b is an isolated view on an enlarged scale taken from FIG. 10a;

FIG. 11b is an isolated view on an enlarged scale taken from FIG. 11a;

FIG. 12 is an exploded view of the tampon applicator of FIG. 11a;

FIG. 13a is a side view of the tampon applicator as in FIG. 11a;

FIG. 13b is a sectional view taken along line 13b-13b of FIG. 13a;

FIG. 14b is an isolated view on an enlarged scale taken from FIG. 14a;

FIG. 15 is an exploded view of the tampon applicator of FIG. 11a;

FIG. 16a is a side view of the tampon applicator as in FIG. 14a;

FIG. 16b is a sectional view taken along line 16b-16b of FIG. 16a.

DESCRIPTION OF THE PREFERRED EMBODIMENT

Figure 1:
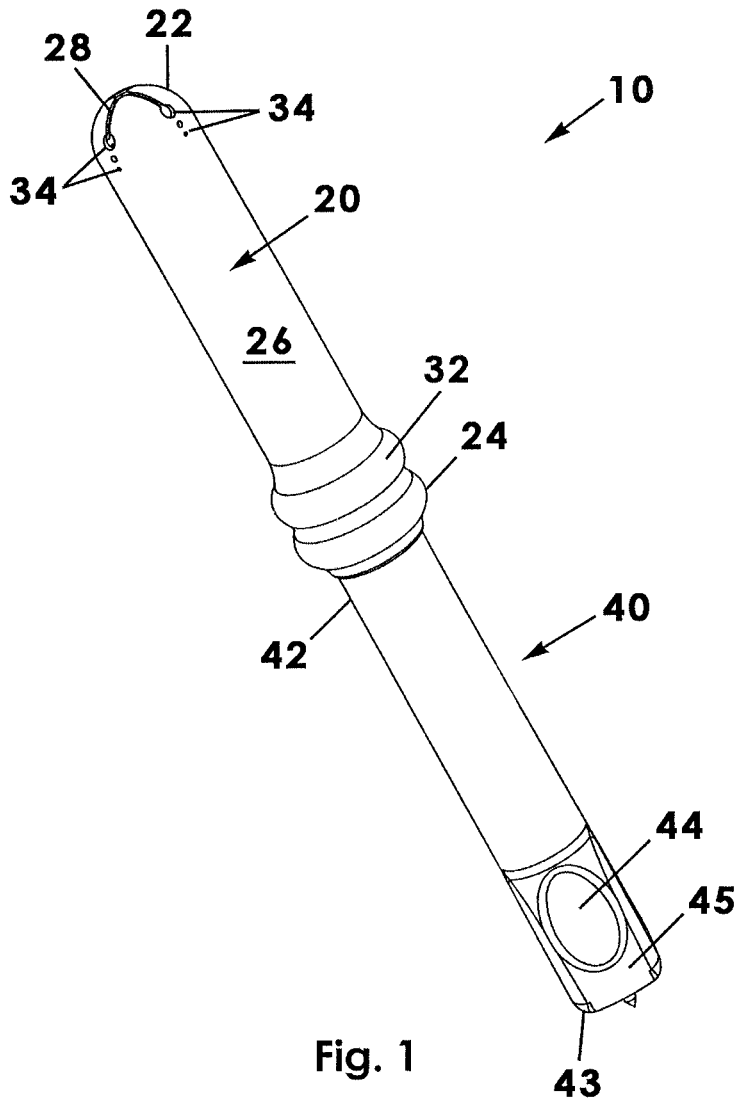
FIG. 1 is a perspective view of an embodiment of a self-lubricating tampon applicator according to the present invention.
Figure 2:
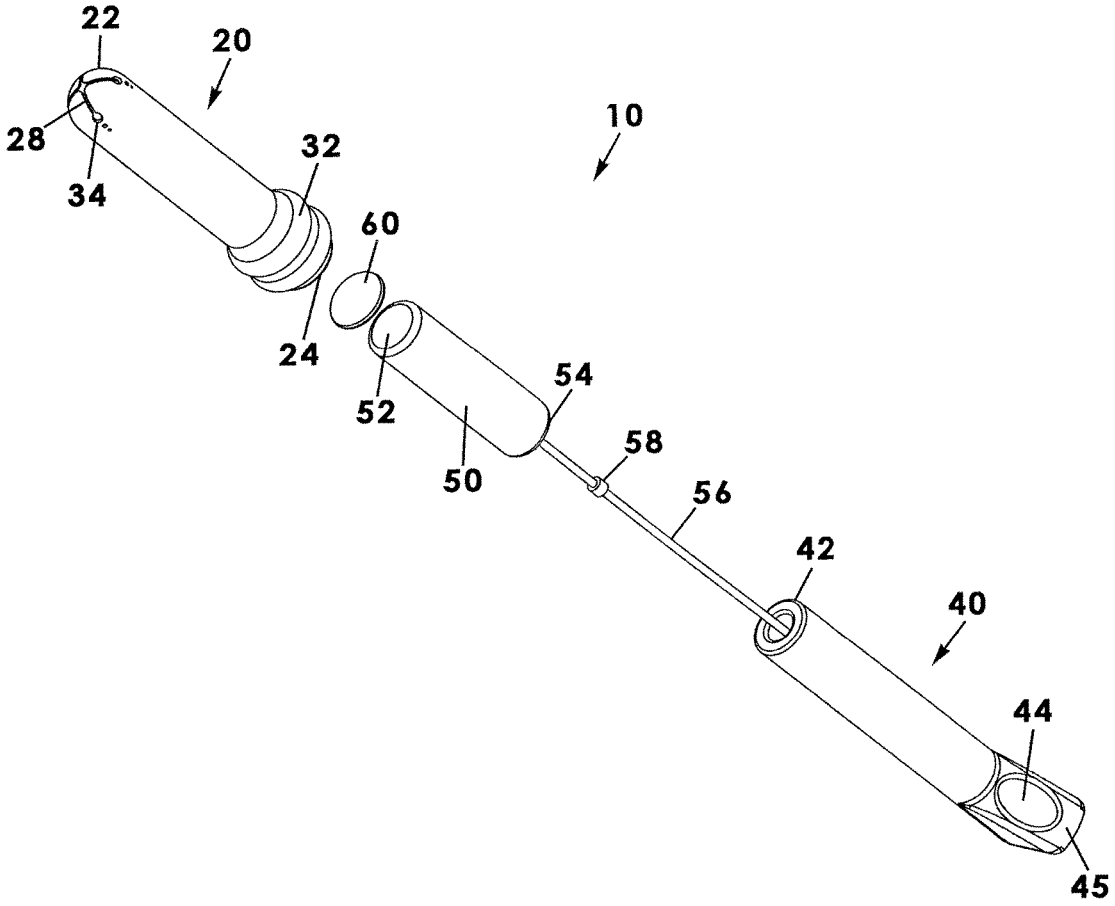
FIG. 2 is an exploded view of the tampon applicator as in FIG. 1.

A self-lubricating tampon applicator according to a preferred embodiment of the present invention will now be described in detail with reference to FIGS. 1 to 16b of the accompanying drawings. The self-lubricating tampon applicator 10 includes a barrel 20, a tampon 50 initially positioned in the barrel 20 defining a lubricant aperture 34, a plunger 40 for pushing the tampon 50 out of the barrel, a lubricant reservoir 60 situated inside the barrel 20, and at least one piercing member 70 for piercing the lubricant reservoir when pressure is applied to the plunger 40 and tampon 50, the lubricant being urged through the lubricant aperture onto an exterior surface of the barrel 20.

The barrel 20 has an insertion end portion 22 and a proximal end portion 24 opposite the insertion end portion 22. While the proximal end portion 24 defines an open end, the insertion end portion 22 is initially closed but then open up as a tampon 50 is pushed out as will be described later. A continuous side wall 26 extends between the proximal end portion 24 and the insertion end portion 22, the continuous side wall 26 having a cylindrical configuration that defines an interior area into which other components are situated and some of which move slidably as will be described.

The insertion end portion 22 includes a two or more (also referred to as a plurality) of lines of separation 28 that divides the insertion portion into a plurality of flaps 30 or panels. Initially, the plurality of flaps may have a curved end or domed configuration that limit access to the interior area (FIG. 1) but that separate to form or define an open end when the tampon 50 is pushed downstream and out of the interior area of the barrel 20 (FIG. 4), as will be described in more detail below.

Figure 3A:
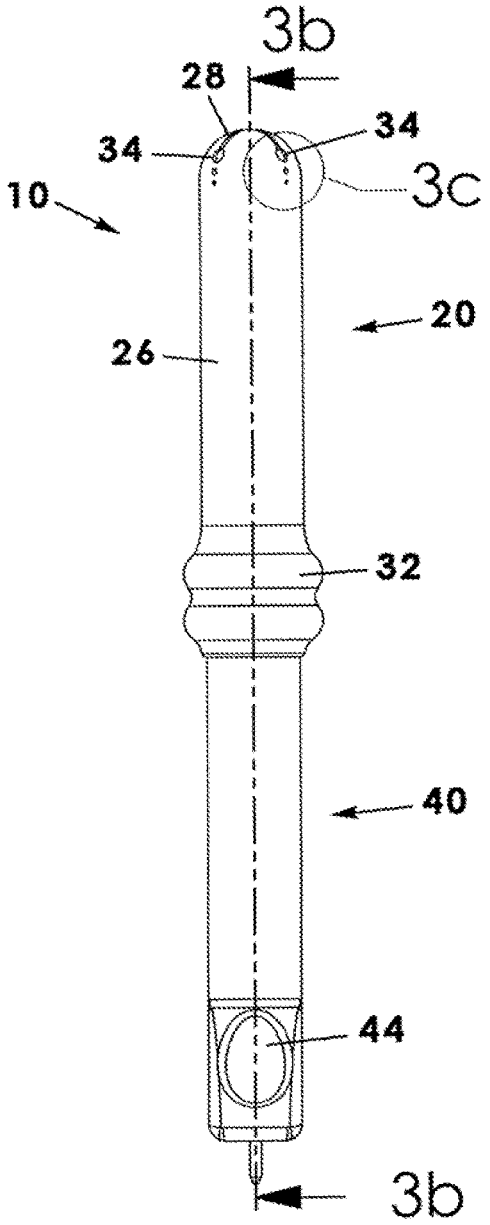
FIG. 3a is a side view of the tampon applicator as in FIG. 1 in a start configuration.
Figure 3C:
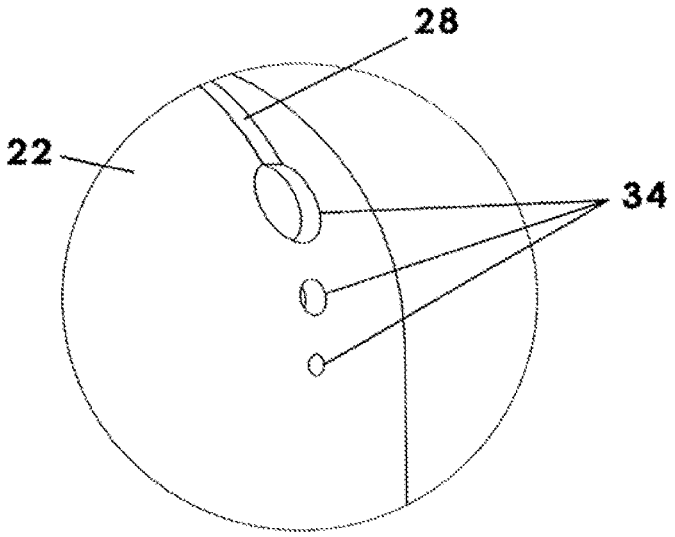

The continuous side wall 26 may define an aperture 34 through which lubricant may be dispensed, the aperture 34 operably communicating the interior area with areas outside of the barrel 20. The aperture 34 may also be referred to as a vent or vent opening through which lubricant may be urged outwardly onto the outer surface of the continuous side wall 26 of the barrel 20. Preferably, the aperture 34 is positioned proximate or adjacent to the insertion end portion 22 (FIGS. 3a and 3c). In an embodiment, the aperture 34 may be a plurality of spaced apart apertures and situated adjacent lower ends of each line of separation 28, respectively. The plurality of apertures 34 may include apertures having a diameter different than a diameter of an adjacent aperture so that different amounts of lubricant will be dispensed therethrough. Other arrangements or grouping of apertures are also contemplated as will be described later.

Figure 6:
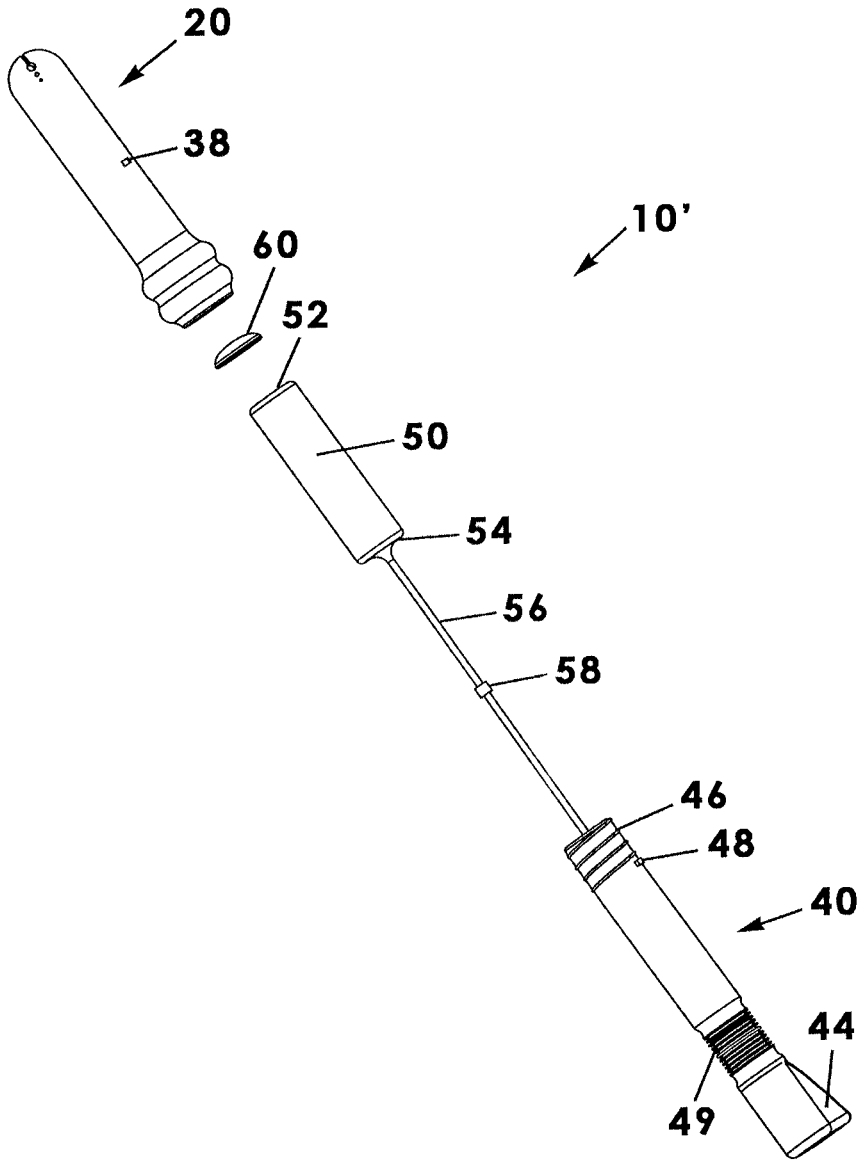
FIG. 6 is an exploded view of the tampon applicator of FIG. 4.
Figure 7A:
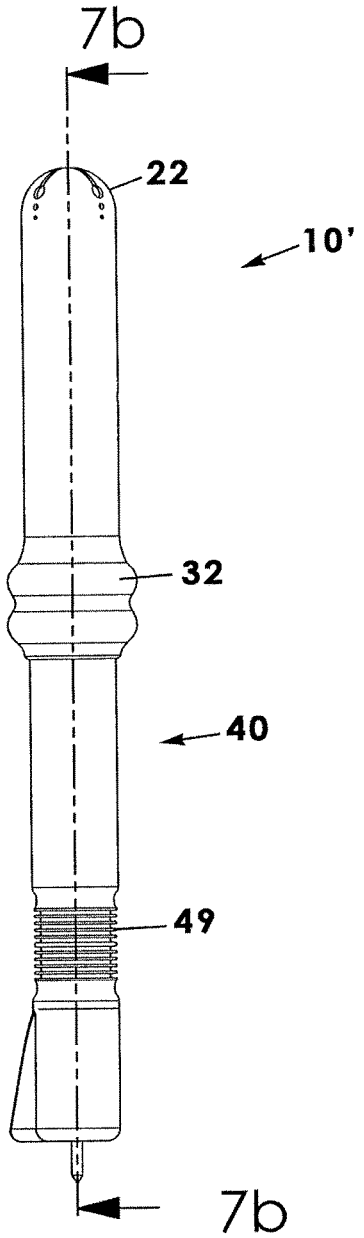
FIG. 7a is a side view of the tampon applicator of FIG. 4 illustrated in an extended or starter configuration.
Figure 7B:
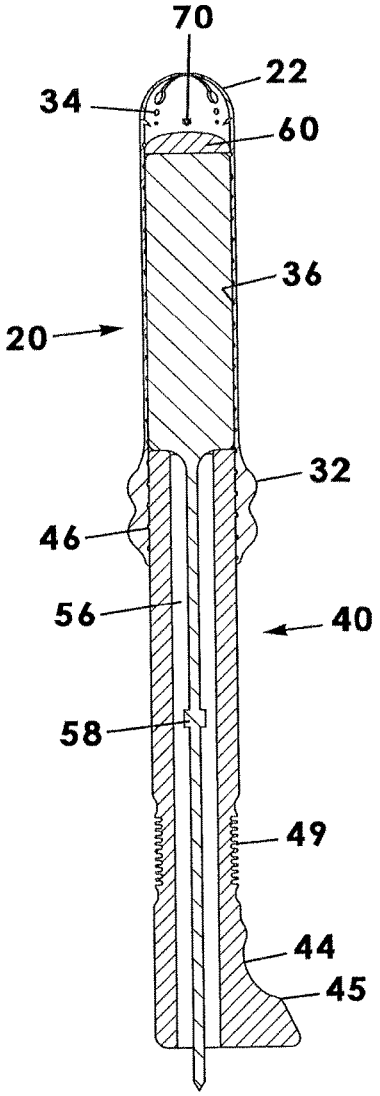

Further, the tampon 50 is initially positioned within the interior area of the barrel 20 and is configured to move slidably when pushed or urged downstream by operation of the plunger 40. The tampon 50 may be constructed or cotton or a blend of materials suitable to absorb blood and other fluids common to a woman's menstrual period. More particularly, the tampon 50 may have a cylindrical configuration with a flat or truncated distal end 52 (i.e. the upper end). Further, the tampon 50 may include a proximal end 54 opposite the distal end 52 from which a string 56 extends (FIG. 6). The string 56 enables a user to extract the tampon 50 more efficiently. Uniquely, the tampon 50 may include a wax plug 58 coupled to or situated along the string 56, the wax plug 58 being constructed of an absorbent material to further eliminate blood or other fluids from leaking from the tampon 50 itself. Alternately, the wax plug 58 may be constructed of a material that simply prevents fluid from passing thereby.

Next, the reservoir 60 (also referred to as a lubricant reservoir) includes a frangible membrane that initially contains a quantity of lubricant and is positioned in the interior area of the barrel. In an embodiment, the reservoir 60 is positioned atop the distal end 52 of the tampon 50 and is movable as the tampon 50 is moved. The membrane of the reservoir 60 is strong enough not to break spontaneously, in a box or other package during purchase, or when being handled during use. However, the membrane of the reservoir 60 is thin enough to be punctured when pushed into contact with one or more piercing members 70.

Figure 3D:
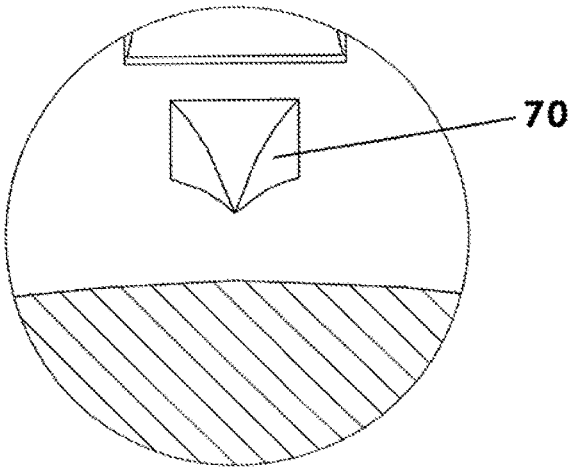

At least one piercing member 70 is fixedly mounted in the interior area of the barrel 20 proximate the aperture 34 and reservoir 60. More particularly, the piercing member 70 is located between the reservoir 60 (when the tampon 50 is in its starting position) and the aperture 34 (FIG. 3b). The piercing member 70 may be in the form of a tooth or sharp hook and include a pointed end (FIG. 3d). In an embodiment, the piercing member 70 may include a plurality of piercing members 70 with each piercing member being spaced apart laterally from an adjacent piercing member 70. It is understood that the piercing members 70 being distributed laterally facilitates a thorough and uniform puncturing of the reservoir 60 when it is urged upwardly by the downstream movement of the tampon 50 as will be described later.

Figure 4:
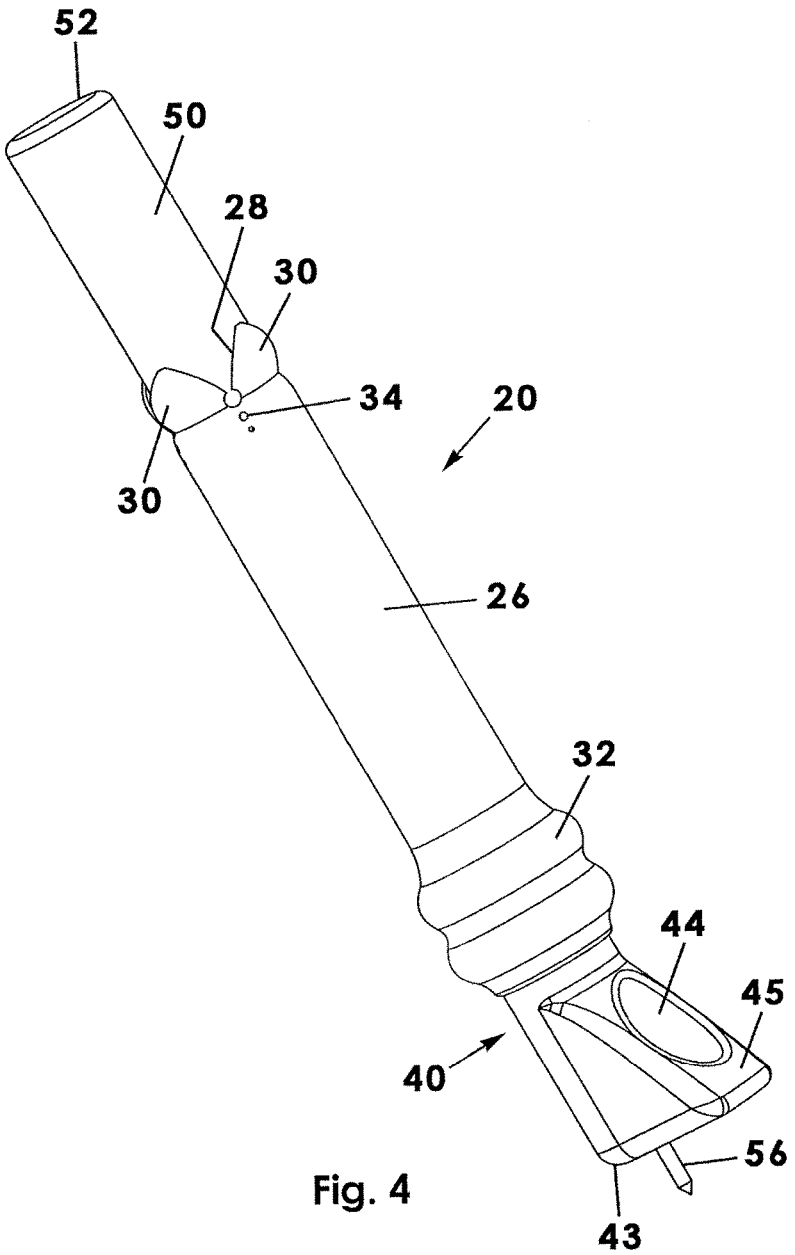
FIG. 4 is a perspective view of an embodiment of a self-lubricating tampon applicator according to the present invention illustrated in a start configuration.
Figure 5A:
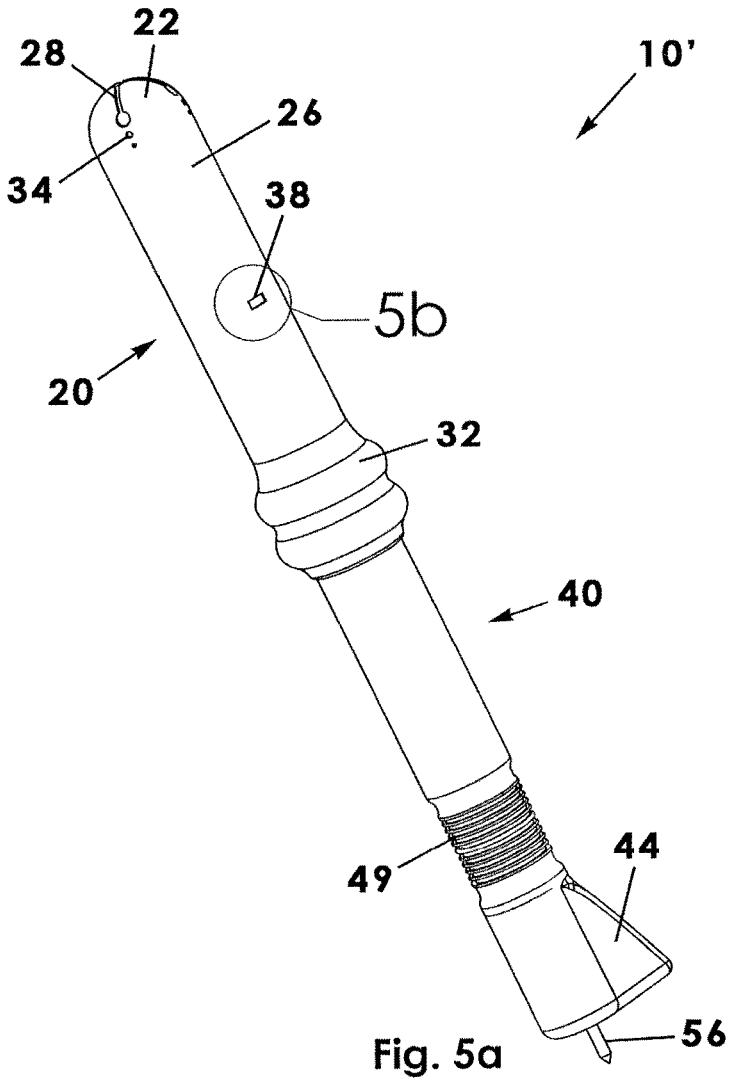
FIG. 5a is another perspective view of the tampon applicator shown in FIG. 4, illustrated in partially deployed configuration.
Figure 5B:
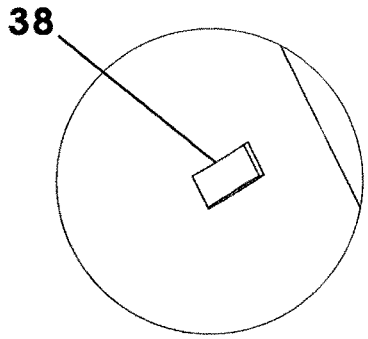

The self-lubricating tampon applicator 10 includes a plunger 40 configured to move slidably in the barrel 20. More particularly, the plunger 40 may have a tubular or cylindrical configuration that enters the barrel 20 via the proximal end portion 24 and has a first end 42 (i.e. the upper end as illustrated) that engages and bears against a lower end of the tampon 50. The plunger 40 is configured to move downstream toward the insertion end portion 22 when pressure is applied thereto by the hand of a user, downstream movement of the tampon 50 urging the reservoir 60 downstream where it bears against the piercing member 70. In an embodiment, the plunger 40 may be pushed downstream in the barrel and moves slidably. The piercing member 70, then, causes the reservoir to be pierced so that lubricant is pushed through respective apertures 34 as the plunger 40 continues to be pushed by the user. Continued pressure on the plunger 40 causes the tampon to be pushed out of the insertion end portion 22 (FIG. 4).

In another aspect, the barrel 20 may include a grip member 32 adjacent the proximal end portion 24 and having a tactile configuration for enhancing the grip of a user's fingers when manipulating the applicator. For instance, the grip member 32 may include a plurality of ridges, nubs, or a rough surface. In addition, the plunger 40 includes a finger guide member 44 is proximate or integrated with a second end 43 (i.e. lower end as illustrated) of the plunger 40, the finger guide member 44 defining an inwardly recessed area having an outwardly extending lower ledge 45 (FIG. 3b) having a shape configuration that, together, selectively receive a finger of a user, enabling a user to keep her hand steady when manipulating the plunger 40.

In another aspect, the barrel 20 may include one or more nubs configured to make a "clicking" sound when impacted by the first end 42 of the plunger 40 as the plunger 40 is moved downstream in the barrel 20. The audible sound provided by the nubs is intended to enable a user to have an awareness of how far the tampon 50 has been inserted and when the plunger 40 and barrel 20 may be withdrawn, leaving the tampon 50 properly deployed. More particularly, a first nub [46] *41* or first set of spaced apart nubs may extend inwardly from an inner surface of the side wall of the barrel 20 and positioned about midway between ends of the barrel 20, i.e. extending into the interior area defined by the side wall. The upstream side of the first nub [46] *41* may be rounded so as not to stop slidable movement of the plunger 40 but includes a construction that may deform or be movable to provide a clicking sound as the plunger 40 passes thereover. An exemplary configuration of a nub is shown in FIG. 3e, it being understood that other shape configurations are possible. Similarly, a second nub 47 or second set of spaced apart nubs 47 may be positioned proximate the insertion end portion 22 and extending inwardly from the side wall of the barrel 20 so as to audibly interact with the first end 42 of the plunger 40 when the plunger 40 is fully deployed into the barrel 20 (FIG. 4).

In an embodiment, the plunger 40 moves downstream through the interior area of the barrel 20 rotationally along complementary threads rather than by sliding as first described above. An embodiment of the self-lubricating tampon applicator 10' will now be described with reference to FIGS. 5a to 10b and is substantially similar to the embodiment first described above except as specifically described below. Primed reference numerals will be used to reference corresponding structures previously described.

Figure 8A:
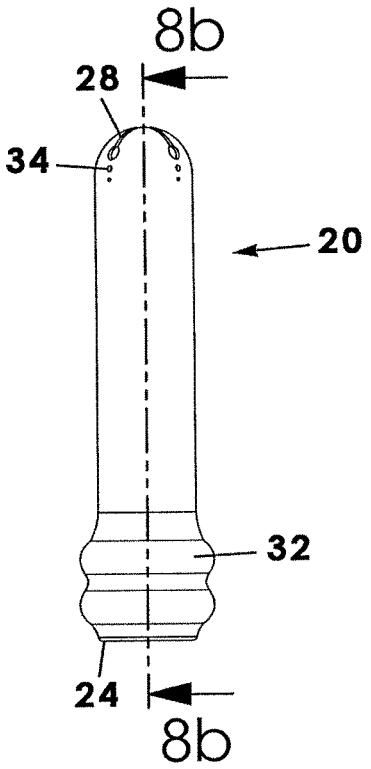
FIG. 8a is a side view of the tampon applicator of FIG. 4 illustrated in deployed configuration.
Figure 8B:
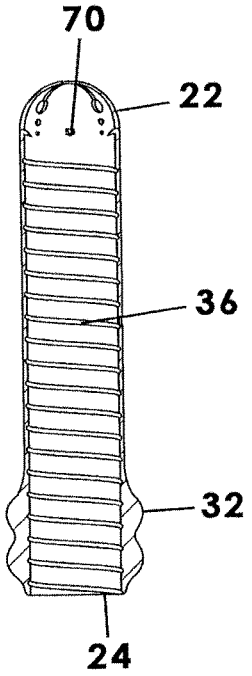
Figure 9:
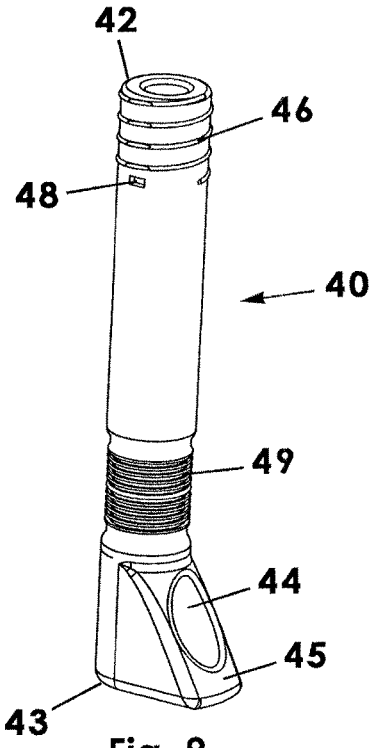
FIG. 9 is an isolated perspective view of the plunger removed from the tampon applicator as in FIG. 4.

More particularly, an inner surface of the continuous side wall 26 of the barrel 20 includes a plurality of threads 36 extending between the proximal end portion 24 and the insertion end portion 22 of the barrel 20 (FIG. 8b). Further, an exterior surface of the plunger 40 includes a threaded portion 46 adjacent the upper end thereof (FIG. 9). The threads of the threaded portion 46 and threads of the plurality of threads 36 have a complementary or inversely identical configuration such that the plunger 40 is moved rotationally downstream in said barrel 20 when the threaded portion 46 is engaged with the plurality of threads and the plunger is manually rotated by a user. An additional set of threads 49 may be included at lower extent of the plunger 40 to enhance the grip of a user while twisting or rotating the plunger 40.

Figure 10A:
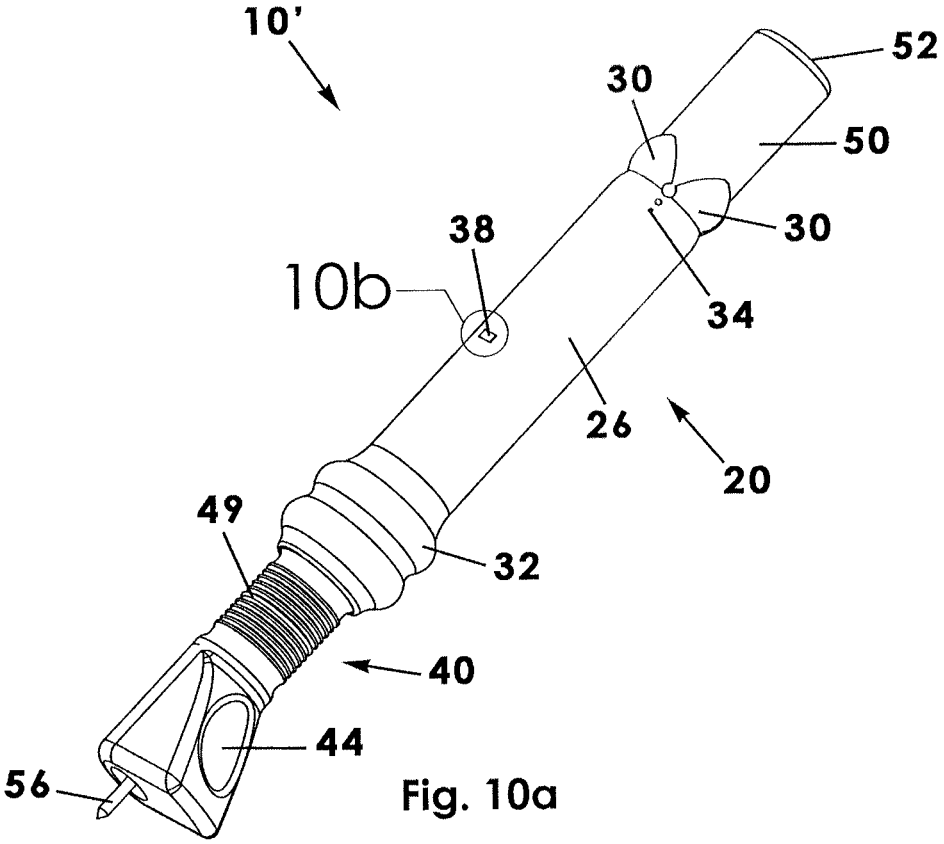
FIG. 10a is a perspective view of the tampon applicator as in FIG. 4, illustrated in a partially deployed configuration.
Figure 10B:
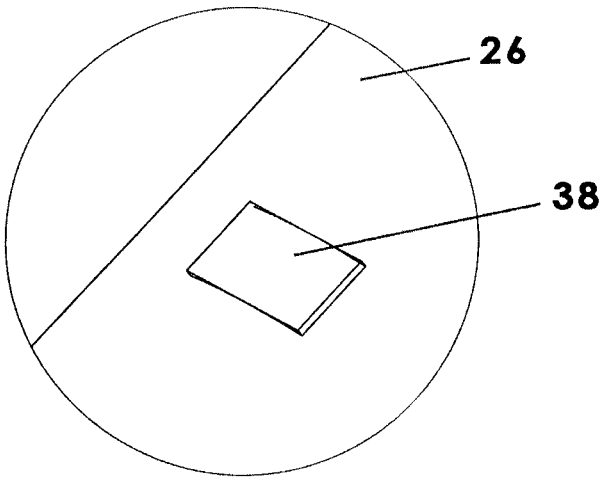

Rotation of the plunger 40, however, is limited; in other words, the plunger 40 is configured to move downstream a predetermined distance in the barrel 20 but then movement is stopped. More particularly, an exterior surface of the plunger 40 includes a flange 48 (which may be described as a nub, button, or a stop). Correspondingly, the continuous side wall 26 of the barrel 20 includes a receiving member 38 positioned and configured to selectively receive the flange 48 when rotation of the plunger 40 aligns the flange 48 and receiving member 38. As shown in the accompanying drawings, the receiving member 38 is an aperture defined by the continuous side wall 26 and having a dimension that is complementary to a dimension of the flange 48 so as to receive the flange 48 therethrough when the nub and aperture are registered (i.e. aligned) with one another. The flange 48 may snap or click into the receiving member 38 in a friction fit or snap-fit arrangement and, as a result, prevent further rotation of the plunger 40 (FIGS. 10 and 10b).

Figure 11A:
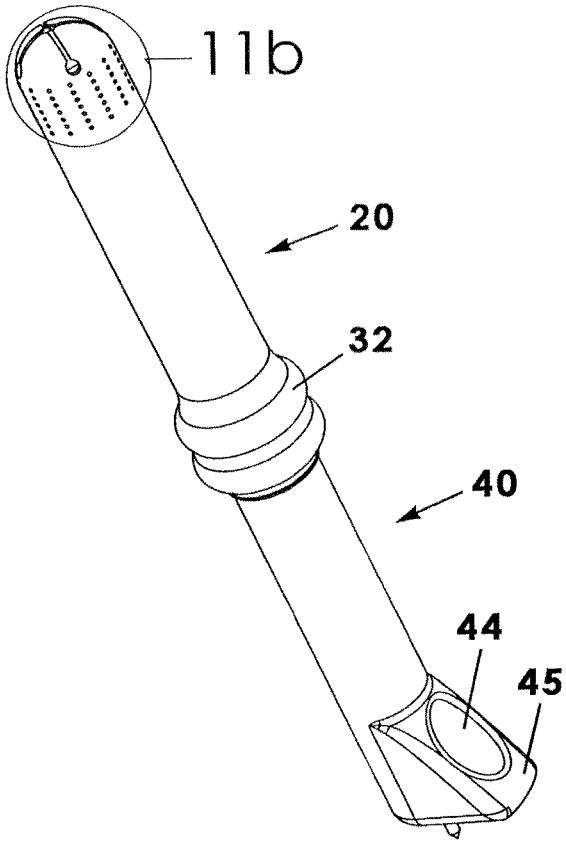
FIG. 11a is a perspective view of an embodiment of a self-lubricating tampon applicator according to the present invention illustrated in a start configuration.
Figure 11B:
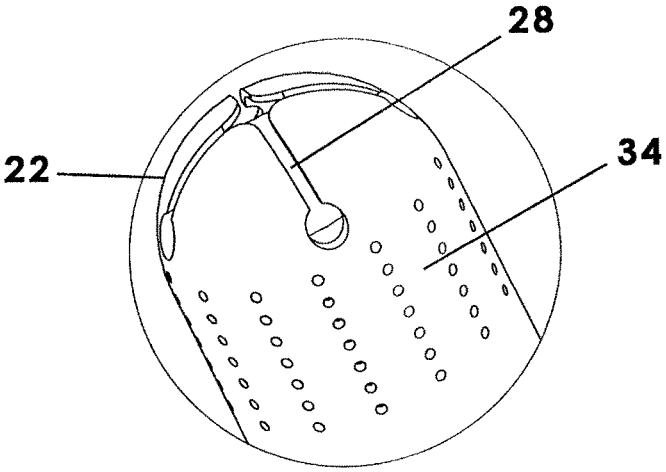
Figure 12:
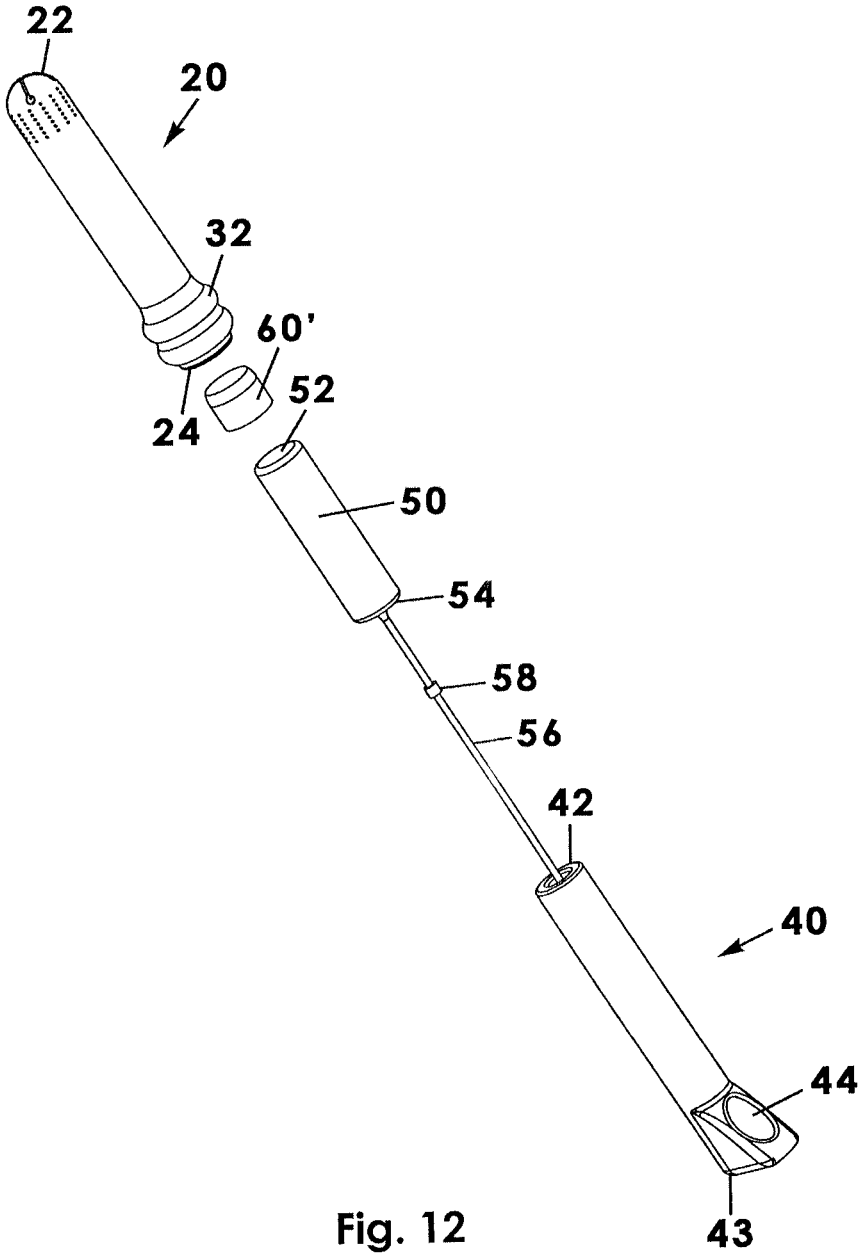

Now, further reference is made to the plurality of apertures 34 and lubricant reservoir 60. In an embodiment, the plurality of apertures 34 (i.e. lubricant vents) may be arranged in a plurality of aperture groups each having multiple apertures aligned in a linear pattern (FIG. 11b). Each aperture group may be spaced apart from and parallel to an adjacent aperture group and situated proximate the flaps 30 of the insertion end portion 22 of the barrel 20. The aperture groups extend away from the insertion end portion 22 or, stated another way, parallel to a longitudinal axis defined by the barrel 20. The aperture groups may be arranged radially about the barrel 20 so that lubricant dispensed from a pierced reservoir is evenly dispensed and distributed onto the external surface of the continuous side wall 26 of the barrel 20. It is understood that reference numeral 34 refers to both a single aperture and the plurality of apertures shown in the accompanying drawings.

Figure 13A:
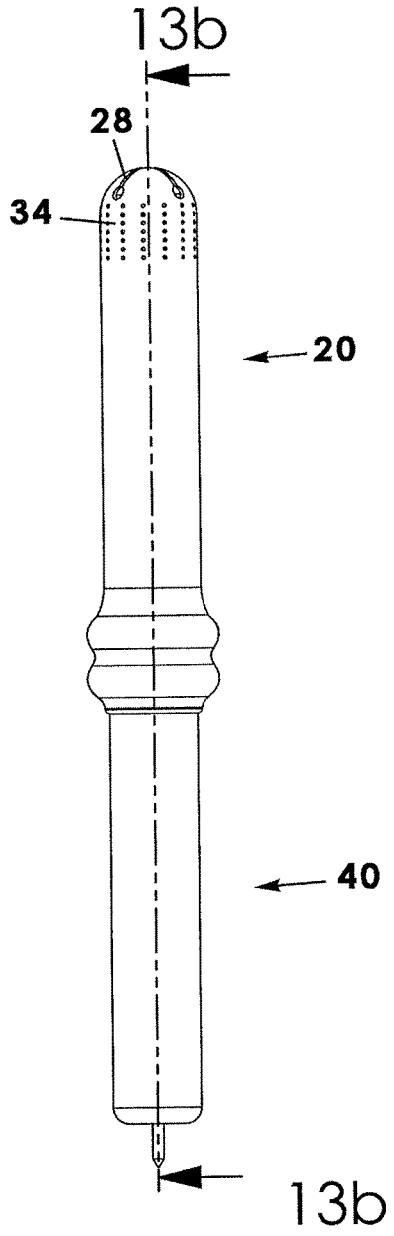
Figure 13B:
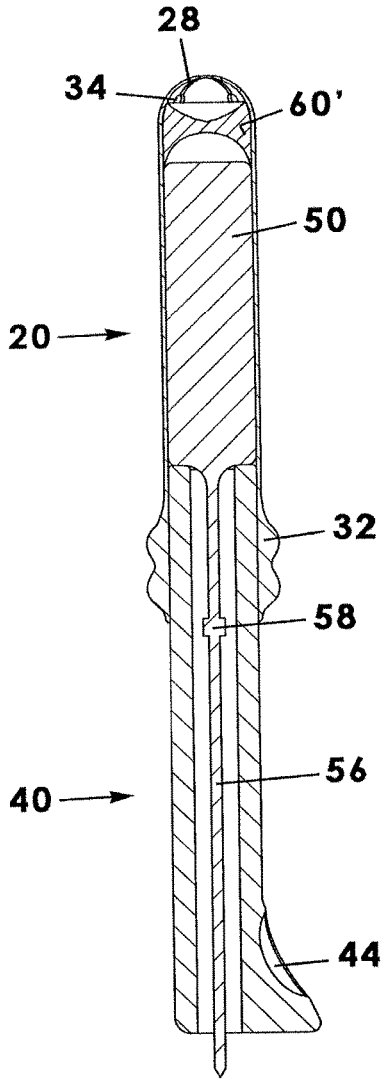
Figure 14A:
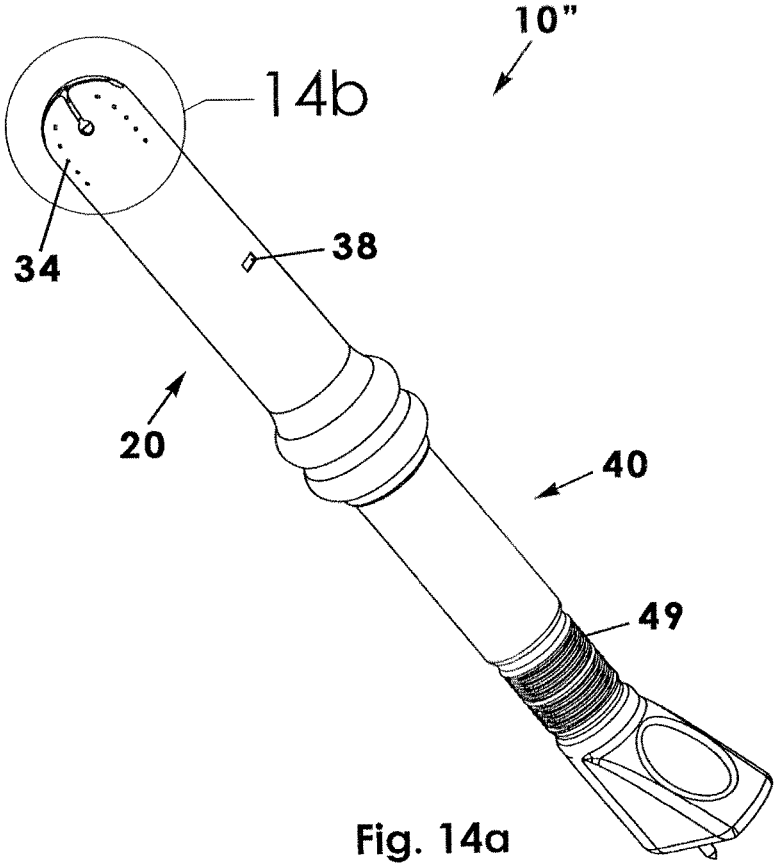
FIG. 14a is a perspective view of the tampon applicator according to another embodiment of the present invention.
Figure 14B:
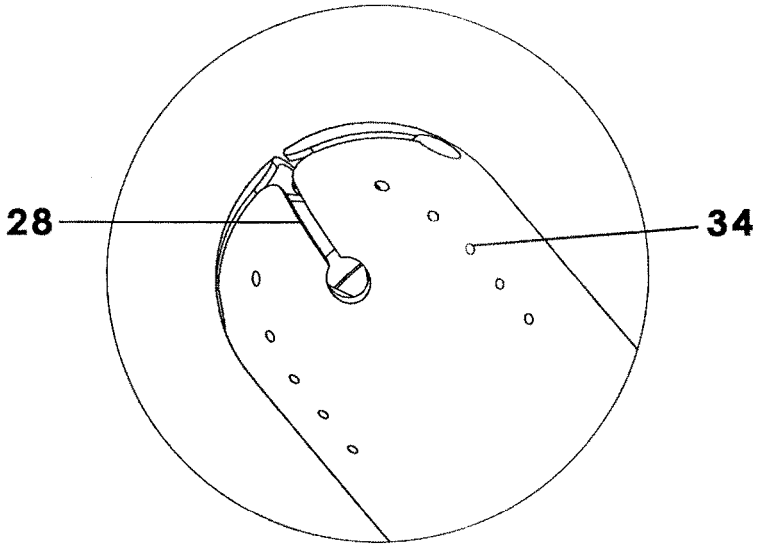
Figure 15:
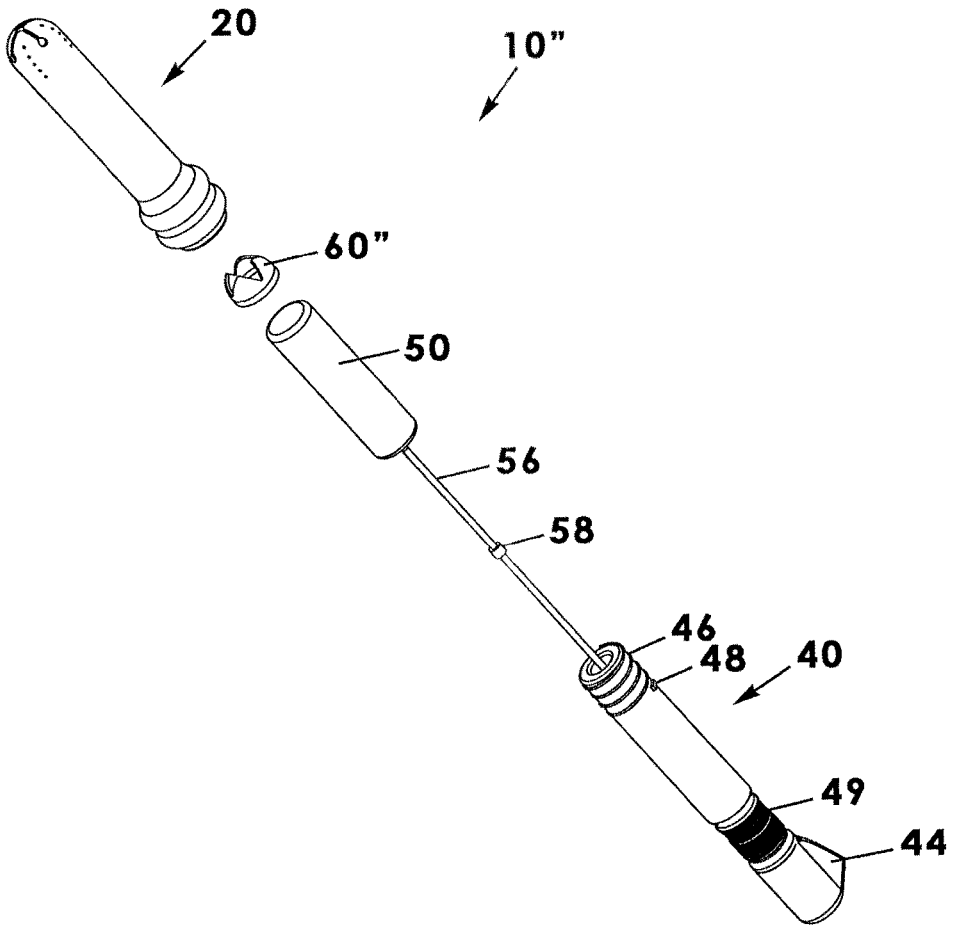

In an embodiment, the reservoir 60' containing lubricant is in simultaneous communication with each of the plurality of apertures 34 so that the lubricant is dispensed through all of the apertures simultaneously when the reservoir 60' is pierced when it impacts the piercing member 70 as described above. In other words, the reservoir 60' may include a spacer that rests atop the tampon 50 so that the lubricant portion thereof bears against the plurality of apertures 34 (FIG. 13b).

Figure 16A:
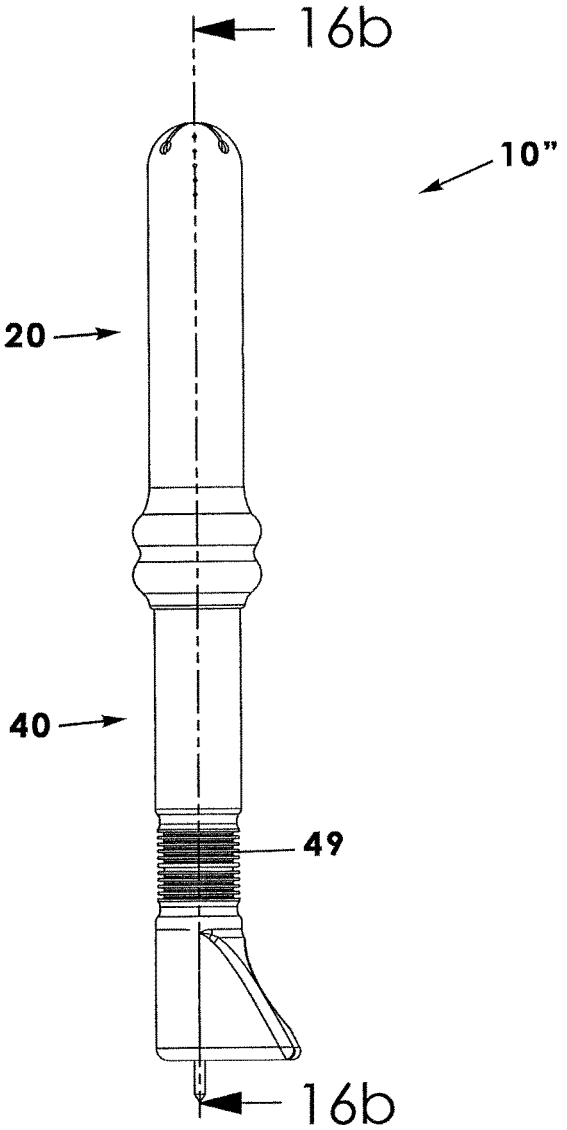
Figure 16B:
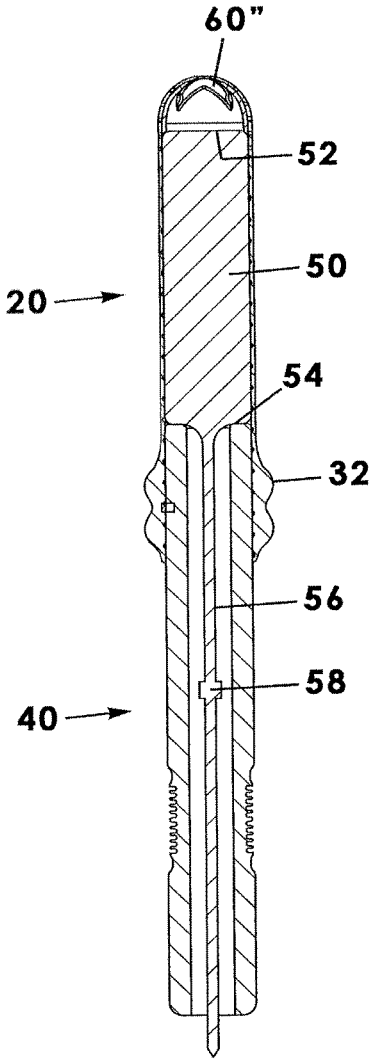

Another embodiment of the self-lubricating tampon applicator 10" is shown in FIGS. 14a to 16b and includes a construction substantially similar to the configurations discussed above except as set forth below. In this embodiment, the reservoir 60" containing lubricant has a configuration complementary to the flaps 30 of the insertion end portion 22 and is positioned to bear against them or be closely proximate to them (FIGS. 16a and 16b).

In use, a human user may push or rotate the plunger 40 upwardly into the barrel 20 so as to urge the tampon 50 upwardly, i.e. downstream. This action, then, causes the reservoir 60 containing lubricant to be pierced by the piercing member 70. The lubricant is then dispensed through the plurality of apertures 34 onto the outer surface of the continuous side wall 26 of the barrel 20 so as to lubricate entry of the applicator 10 into the vagina of the user. The specific position of the piercing member 70, reservoir 60, and aperture 34 enable the lubricant to be dispensed onto the outer surface of the barrel 20 simultaneously with extension of the tampon 50 through the insertion end portion 22 of the barrel 20.

It is understood that while certain forms of this invention have been illustrated and described, it is not limited thereto except insofar as such limitations are included in the following claims and allowable functional equivalents thereof.

The invention claimed is:

1. A self-lubricating tampon applicator, comprising:

a barrel having an insertion end portion and a proximal end portion opposite said insertion end portion and having a continuous side wall extending therebetween that defines an interior area;

wherein said continuous side wall defines an aperture adjacent said insertion end portion;

a tampon initially positioned in said interior area of said barrel;

[wherein said tampon includes a string extending from a proximal end thereof to enable removal of said tampon after deployment;]

a piercing member positioned in said interior area intermediate said tampon and said aperture;

a reservoir containing a lubricant positioned in said interior area between said tampon and said piercing member;

a plunger mounted in said barrel and having a first end engaging a proximal end of said tampon, said plunger having a cylindrical configuration selectively slidable from a starter configuration extending away from the proximal end portion of the barrel to a deployed configuration positioned inside the barrel;

wherein pressure applied to said plunger causes said plunger to urge said tampon and said reservoir downstream within said interior area of said barrel and said reservoir to be pierced by said piercing member, the lubricant from said reservoir being urged through said aperture while simultaneously pushing the tampon out of the barrel into a deployed state;

wherein the plunger and barrel are configured to be withdrawn and separated from the deployed tampon.

2. The self-lubricating tampon applicator as in claim 1, wherein said insertion end portion includes multiple lines of separation configured to separate and define an open end when said plunger is moved toward said deployed configuration.

3. The self-lubricating tampon applicator as in claim 1, wherein said aperture includes a plurality of apertures, each aperture being spaced apart from an adjacent aperture.

4. The self-lubricating tampon applicator as in claim 3, wherein each aperture has a diameter different than a diameter of an adjacent aperture.

5. The self-lubricating tampon applicator as in claim 2, wherein:

said aperture defined by said insertion portion includes a plurality of apertures, each aperture being spaced apart from an adjacent aperture;

said plurality of apertures are positioned rearwardly adjacent each line of separation.

6. The self-lubricating tampon applicator as in claim 3, wherein said plurality of apertures are arranged in a plurality of aperture groups, each aperture group having a rearwardly-extending linear configuration spaced apart from an adjacent aperture group.

7. The self-lubricating tampon applicator as in claim 1, wherein said barrel includes a grip member adjacent said proximal end portion having a tactile configuration for enhancing finger grip of a user.

8. The self-lubricating tampon applicator as in claim 1, wherein said plunger includes a finger guide member coupled to a proximal end thereof, said finger guide member having a shape configuration for selectively receiving a finger of a user, whereby to steady operation of said plunger.

9. The self-lubricating tampon applicator as in claim 1, wherein said tampon includes *a string extending from a proximal end thereof to enable removal of said tampon after deployment and includes* a wax plug constructed of an absorbent material situated along said string to resist passage of liquid thereby.

10. The self-lubricating tampon applicator as in claim 1, further comprising a first nub extending inwardly from an inner surface of said barrel, said nub having a construction that produces an audible sound when impacted by said first end of said plunger while moving toward said deployed configuration.

11. The self-lubricating tampon applicator as in claim 1, wherein:

an inner surface of said continuous side wall of said barrel defines a plurality of threads between said proximal end portion and said insertion end portion;

an exterior surface of said plunger defines a threaded portion complementary to said plurality of threads of said continuous side wall causing downstream movement of said plunger within said interior area of said barrel when engaged.

12. The self-lubricating tampon applicator as in claim 11, wherein:

said exterior surface of said plunger includes a nub;

said barrel defines a receiving member selectively receiving said flange after a predetermined downstream movement of said plunger in said barrel, receipt of said flange by said receiving member preventing further downstream movement of said plunger.

13. The self-lubricating tampon applicator as in claim 12, wherein said receiving member is an opening defined by said continuous side wall having a dimension complementary to a dimension of said nub for receiving said nub in a friction fit engagement.

14. The self-lubricating tampon applicator as in claim 1, wherein:

said aperture includes a plurality of apertures, each aperture being spaced apart from an adjacent aperture;

said piercing member includes a plurality of piercing members, each piercing member being spaced apart from an adjacent piercing member and including a tooth proximate a respective aperture.

15. The self-lubricating tampon applicator as in claim 14, wherein said reservoir is positioned immediately atop said tampon and configured to dispense the lubricant when pierced by said piercing member.

16. The self-lubricating tampon applicator as in claim 14, wherein:

said plurality of apertures is arranged in a plurality of aperture groups, each aperture group having a linear configuration spaced apart from an adjacent aperture group;

said reservoir has a configuration that is in communication with said plurality of apertures before being pierced so that the lubricant is dispensed through said plurality of apertures simultaneously when said reservoir is pierced by said piercing member.

17. The self-lubricating tampon applicator as in claim 1, wherein:

said insertion end portion includes multiple lines of separation configured to separate said insertion end portion into a plurality of flaps that define an open end when said plunger is moved toward said deployed configuration;

said reservoir has a configuration complementary to a configuration of said plurality of flaps and is positioned to bear against said plurality of flaps.

18. A self-lubricating tampon applicator, comprising:

a barrel having an insertion end portion and a proximal end portion opposite said insertion end portion and having a continuous side wall extending therebetween that defines an interior area, said continuous side wall defining a plurality of apertures spaced apart from one another and proximate said insertion end portion;

a tampon positioned initially in said interior area of said barrel;

a [plurality of] piercing [members] *member* fixedly coupled to an inner surface of said continuous side wall and [spaced apart from one another] *positioned* in said interior area between said tampon and said plurality of apertures;

a reservoir containing a lubricant positioned in said interior area between said tampon and said [plurality of] piercing [members] *member*;

a plunger operably situated in said barrel having a first end engaging a proximal end of said tampon, said plunger having a cylindrical configuration selectively slidable from a starter configuration extending away from said proximal end portion of said barrel to a deployed configuration positioned in said interior area of said barrel;

wherein pressure applied to said plunger pushes said tampon and said reservoir downstream within said interior area of said barrel and said reservoir is pierced by said piercing member, whereby the lubricant from said reservoir is dispensed through said plurality of apertures onto an outer surface of said barrel while simultaneously pushing the tampon out of the barrel into a deployed state;

wherein the plunger and barrel are configured to be withdrawn and separated from the deployed tampon.

19. The self-lubricating tampon applicator as in claim 1, wherein said insertion end portion includes multiple lines of separation configured to separate and define an open end when said plunger is moved toward said deployed configuration.

20. The self-lubricating tampon applicator as in claim 18, wherein said plurality of apertures are arranged in a plurality of aperture groups, each aperture group having a rearwardly-extending linear configuration spaced apart from an adjacent aperture group.

21. The self-lubricating tampon applicator as in claim 18, wherein said plunger includes a finger guide member coupled to a proximal end thereof, said finger guide member having a shape configuration for selectively receiving a finger of a user, whereby to steady operation of said plunger.

22. The self-lubricating tampon applicator as in claim 18, wherein:

an inner surface of said continuous side wall of said barrel defines a plurality of threads between said proximal end portion and said insertion end portion;

an exterior surface of said plunger defines a threaded portion having a pattern of threads complementary to said plurality of threads of said continuous side wall causing downstream movement of said plunger within said interior area of said barrel when said plunger is moved from said starter configuration toward said deployed configuration.

23. The self-lubricating tampon applicator as in claim 18, wherein:

said exterior surface of said plunger includes a flange;

said barrel defines a receiving member selectively receiving said flange after a predetermined downstream movement of said plunger in said barrel, receipt of said flange by said receiving member preventing further downstream movement of said plunger.

* * * * *